United States Patent
Weber et al.

(10) Patent No.: US 6,726,693 B2
(45) Date of Patent: *Apr. 27, 2004

(54) TISSUE RESURFACING USING BIOCOMPATIBLE MATERIALS

(75) Inventors: Paul J. Weber, Ft. Lauderdale, FL (US); Luiz B. Da Silva, Danville, CA (US); Alexander M. Rubenchik, Livermore, CA (US)

(73) Assignee: Pearl Technology Holdings, LLC, Livermore, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/820,131

(22) Filed: Mar. 28, 2001

(65) Prior Publication Data

US 2002/0058952 A1 May 16, 2002

Related U.S. Application Data (63) Continuation-in-part of application No. 09/710,478, filed on Nov. 10, 2000.

(51) Int. Cl.⁷ .............................................. A61B 17/50
(52) U.S. Cl. ........................... 606/131; 604/291; 451/75
(58) Field of Search ................... 606/131, 20; 604/290, 604/291; 451/39, 75

(56) References Cited

U.S. PATENT DOCUMENTS

| | | | | |
|---|---|---|---|---|
| 4,703,590 A | * | 11/1987 | Westergaard | |
| 5,616,067 A | * | 4/1997 | Goenka | 451/39 |
| 5,779,523 A | * | 7/1998 | Mesher | 451/93 |
| 5,820,447 A | * | 10/1998 | Niechcial | 451/99 |
| 5,910,042 A | * | 6/1999 | Niechcial | 451/39 |
| 5,913,711 A | * | 6/1999 | Visaisouk | 451/39 |
| 5,971,999 A | * | 10/1999 | Naldoni | 606/131 |
| 6,080,165 A | * | 6/2000 | DeJacma | 606/131 |
| 6,141,985 A | * | 11/2000 | Cluzeau et al. | 62/293 |
| 6,174,225 B1 | * | 1/2001 | Becker | 451/75 |
| 6,226,996 B1 | * | 5/2001 | Weber et al. | 62/126 |
| 6,306,119 B1 | * | 10/2001 | Weber et al. | 604/290 |

FOREIGN PATENT DOCUMENTS

| | | | |
|---|---|---|---|
| EP | 0 324 448 A1 | * | 7/1989 |
| EP | 0 564 392 A2 | * | 10/1993 |
| GB | 2 095 538 A | * | 10/1982 |
| WO | WO 97/11650 | * | 4/1997 |
| WO | WO 99/37229 | * | 7/1999 |

* cited by examiner

*Primary Examiner*—Ralph A. Lewis
(74) *Attorney, Agent, or Firm*—John P. Wooldrid (57) ABSTRACT

Tissue resurfacing is accomplished by propelling biocompatible, non-toxic materials at the tissue with sufficient velocity to cause destruction or loosening of tissues to a desired depth. The biocompatible materials are generated by abrading a solid frozen unit and propelling the abraded material onto the surface of the skin or tissue to be treated. A vacuum line near the delivery tip may used to remove excess materials or reaction by-products that build up on the surface of the skin. The treatment system generally consists of a control unit, a handheld particle generator and a cable that connects the control unit to the particle generator. The control unit can include user controls to select particle temperature, particle flux, particle velocity and vacuum. The handheld particle generator contains a mechanism to push the frozen biocompatible material against a rotating grinding wheel that produces small particles, which are propelled against tissue being treated.

39 Claims, 8 Drawing Sheets

TISSUE RESURFACING USING BIOCOMPATIBLE MATERIALS

This is a continuation in part of U.S. patent application Ser. No. 09/710,478, titled "Tissue Removal Using Biocompatible Materials", filed Nov. 10, 2000 and incorporated herein by reference.

BACKGROUND OF THE INVENTION

1. Field of the Invention

The present invention relates to techniques for cleaning, resurfacing or treating human tissue (e.g., skin) using biocompatible materials propelled into the surface of the tissue.

2. Description of Related Art

Resurfacing the human skin can be achieved by several mechanisms that are aimed primarily at disrupting the epidermal and upper dermal layers. Human skin is composed of at least three layers of variable thickness, depending upon body location. The uppermost layer, or epidermis, is usually as thin as a sheet of paper. The layer just below the epidermis is the dermis, which is largely composed of collagen and makes up the "leather" layer of the skin. The dermis may vary in thickness from that of paper (50–100 $\mu$m) to as thick as half an inch on the neck and back. The layer below the dermis may be composed of either muscle (around the eyes and mouth) or fat, otherwise known as subcutaneous fat New human surface skin is regenerated following resurfacing by the surrounding islands of normal epidermis and epidermal cells migrating from the deep hair pores and other pore structures that permeate the upper dermis, mid dermis, and epidermis. If excessive scar tissue, rather than a plethora of epidermal cells, closes a surface wound, then an unsightly scar will result. The key to all resurfacing procedures is a controlled destruction of the desired area that still allows the regeneration of new tissues from pores and neighboring islands of untouched, untreated skin.

The procedures currently used in human skin resurfacing include chemical peeling, dermabrasion, laser surgery, and most recently the "power peel" or crystalline peel. In chemical peeling, a caustic, disruptive or destructive liquid agent is applied to the surface skin to damage existing epidermal and dermal cells, which will then be replaced by the body. Peeling agents act depending on their strength and type. Examples of chemical peeling agents include fruit acid peel, glycolic acid peel, and trichloracetic acid (TCA) and phenol peels. TCA peels can be made to act at deeper and varying depths by varying the concentration of TCA used to destroy the surface skin. Concentrations as low as 5–10% TCA will behave similarly to a fruit acid peel, and concentrations of 50% TCA may cause severe peeling burns, which simulates phenol, and may border on scarring. Phenol, when diluted with water, penetrates more deeply and destroys more tissue than most other peeling agents.

Dermabrasion literally means abrasion of the skin and is a procedure in which a rotating sanding piece, or abrasive substance, is applied to a rigidified skin to sand out an undesirable feature, mark, or scar. Some high-speed dermabrasion rotors go up to 200,000 revolutions per minute (rpm) and do not require any rigidity to the tissues; however, they require extremely skilled personnel and special instrumentation and are impractical for most office use. A minor mistake with such a high-powered machine can have disastrous results. Dermabrasion is usually performed with a rotating wheel operating at speeds under 10,000 rpm after the skin has been rigidified using freon or dichlorotetrafluoroethane. In dermabrasion (unlike laser surgery), the person operating the abrading wheel has a direct tactile sense of pressing the wheel into the tissues being treated and can apply differential pressure to areas of elevation. Dermabrasion can be achieved to various depths depending upon the depth of freezing (rigidification), the number of passes of the abrader, the type of abrasive wheel, and the pressure applied. This procedure is waning in use, however, due to the unavailability of Freon.

Laser surgery has recently become popular to remove or reduce wrinkles, remove tumors, and alter scars, although results are mixed. Several types of lasers are used, including carbon dioxide and erbium-YAG lasers. Carbon dioxide lasers deliver light radiation at 10 $\mu$m, which can vaporize and destroy surface skin. These lasers may be set on various pulse patterns to deliver precise and controlled amounts of laser radiation to the skin in a relatively uniform and homogenous fashion across the surface. An unfortunate disadvantage of this laser is that heat can be transmitted to the surrounding tissues. Additionally, after the first pass of the carbon dioxide laser, the skin begins to ooze and become wet at the surface as fluids build up in response to the damage. Since water and blood absorb in the infrared region, a second pass of the laser will penetrate to a variable depth, depending on how much surface ooze there is in the area. The ooze prevents the laser energy from reaching the target tissues uniformly. During laser irradiation, the tissues may begin to desiccate, which ultimately results in severe thermal damage. Depositing too much laser energy on the target tissues can result in persistent redness, scarring, and other complications or damage, even with thermal relaxation techniques to mitigate heat transfer.

Although other lasers, such as the erbium-YAG laser or combination $CO_2$/erbium laser, were developed in an attempt to reduce bleeding and thermal damage, serious scarring and persistent redness can still result. If the penetration depth of the damage is complete and the regenerating skin structures are destroyed, scarring will ensue. Scarring is the unwanted presence of large amounts of collagen in the upper surface, with a minimal amount of normal appearing epidermis to lend a normal appearance to the skin. When scars are treated with certain lasers, the light does not actually remove or destroy collagen, but usually affects the hemoglobin and other blood pigments. The reduction of blood vessels to the scar causes an optical effect that makes the scar less noticeable.

Microdermabrasion (MDA) also known as "The Power Peel" is a relatively new treatment patented by Molinari in U.S. Pat. No. 5,037,432. MDA has been used in Europe for the last decade. MDA is a process by which aluminum oxide crystals, which are extremely rigid, strong rasping and irregular-shaped, are projected onto the skin by air that is driven by pressures neighboring 25 pounds per square inch. Safe operation of these devices requires the use of a limited number of passes or a minimal pass speed over the target area. Most power peels are designed to remove the epidermis of the skin. However, epidermal removal will not result in any alteration of scar formation.

Almost all "foreign" objects are unwanted by the body. This also includes particles that are apparently inert such as sand. There are a few problems with aluminum oxide crystals and their use on the face as a peeling agent. If proper depth were attained in order to remove, destroy or alter deeper structures such as scars, pores or pits; then granuloma formation would result from the impact and placement of the aluminum oxide into the structures of the skin and the surrounding skin tissue. This is not wanted and leads to unsightly scarring. There are three main systems, of MDA used in America today; some of the systems come with a vacuum apparatus to partially suck away unwanted particles. The MDA vacuum apparatus sucks most but not all of the crystals passed. Since aluminum oxide crystals can cause foreign body reactions, even a small amount of them could be unwanted or lead to cellular difficulties later on in life. Therefore, since a MDA machine vacuum cannot be made 100 percent efficient, the power peel should not be used at a depth below the epidermis.

Two potentially serious problems have now been proposed regarding MDA. Silicosis or coal miners' lung disease is frequently fatal; sand-like particles are spun into the air (of coal mines) coating the lungs with material that causes delayed foreign body reactions years later and interferes with breathing. In MDA the ultra-fine particles are like miniature sandspurs and are easily inhaled by the patient, thus causing a potential lung disease years from the time of exposure. Additionally, the aluminum oxide particles can deposit on the conjunctiva of the eye latching on and never letting go and causing conjunctivitis (pink eye) that may be permanent A relatively new twist on MDA is to have a separate canister of crystallized vitamins able to be tapped and in the gas flow loop of the aluminum oxide crystals to provide the mechanical "peeling" and some claimed effect of skin vitamin replenishment. Problems have arisen because any humidity in the system causes the powderized vitamins to crystallize or clump, thus clogging the microdermabrasion delivery device. The vitamin or attendant particles also do not impact on the same exact cellular location that the abrasive impacts in this type of delivery system.

WO-9937229 by Coleman et al. discloses propelling water at high speeds and pressures to cut or alter tissues. The use of water as the carrier vehicle has several major drawbacks and disadvantages. As in the time-honored process of dermabrasion (described above), freezing the skin rigid allows controlled application of energy to reduce defects. In order to immobilize skin for uniform abrasion (so that it does not deform or invaginate at treatment) temperatures well below 0 degrees Centigrade are required. Water, even when mixed with large quantities of ice cannot achieve the desired skin-immobilizing temperatures well below 0 degrees (even when not at standard pressure). Additionally, the patent by Coleman et al. would not be effective in delivering chemicals to the skin that could not be miscible with water or in solution with water unless a constant stirring mechanism was included in all portions of the Coleman system; liposomes and oil-soluble materials would separate and likely segregate into a non-uniform spray in the liquid-water-driven Coleman patent. The Coleman system would likely not uniformly expose the dermal layers so that effective application of vitamins and other medicaments could be delivered to even the upper-mid dermal layers of the skin.

Current treatments for skin at risk for infection due to thermal burns, chemical burns or other trauma or disease include removal by "cold steel" otherwise known as scalpel/scissor debridement and more recently by laser. By and large, debridement procedures may be painful if the nerves supplying the living tissues adjacent to the compromised tissue are still functional. This is because for the surgeon to be sure of having removed the devitalized tissues most debridement procedures are performed until bleeding is noticed (a property that is usually indicative that living/good tissue has been reached) thus ensuring that all the dead tissue has been removed. Again, dead tissue is a culture dish, lacking any antibiotics or other medicines that could halt the spread and feeding of infectious organisms.

Tissues that may need to be debrided include the largest organ (skin) following burns from fire, chemicals, blasts, etc. Also included are any exposed and damaged internal components, mostly comprising the muscle and fatty tissues just underlying the skin following blast or kinetic energy trauma. Further included may be open organs from the abdominal cavity following blast injuries, even including the bowel.

The deep but fine firing of biocompatible or bioabsorbable compounds or drugs in an aqueous vehicle, especially antibiotics (antibacterial, antiviral, anti-fungal) onto the human skin, may allow deep treatment of damaged, or devitalized skin and tissue. The device may perform the optimal multiple functions of not only removing unwanted tissues but also leaving behind desirable chemicals/medicines in order to improve the remaining tissues or prevent the growth of unwanted organisms or undesirable tissue reactions.

Thus, it would be advantageous to develop a procedure for removal of scars, wrinkles, and various other imperfections or lesions on the skin, as well as debridement of burns and cleaning of wounds, without introducing foreign bodies or substances that cause adverse physiological reactions or produce thermal damage. The present invention provides such advantages by using materials that are biocompatible.

SUMMARY OF THE INVENTION

The present invention is an apparatus for resurfacing or treating tissue using biocompatible, non-toxic materials that are propelled at the tissue with sufficient velocity to cause destruction or loosening of tissues to the desired depth upon impact. U.S. Pat. No. 6,306,119, titled "Skin Resurfacing and Treatment Using Biocompatible Materials", filed Jan. 20, 1999 is incorporated herein by reference. One objective of the invention is to propel materials into the tissue that are harmonious with the human body and thus do not cause foreign body reactions, which lead to granulomas and scarring. The materials must be hard enough (crystalline) or propelled at high enough velocities to remove tissue. Suitable resurfacing materials include solid carbon dioxide (dry ice), ice (frozen $H_2O$), organic materials such as urea, or other amines (including amino acids) or amides, organic polymers such as sugars, carbohydrates, or proteins, and inorganic salts such as phosphates, sulfates, carbonates and nitrates. To relieve pain, a local anesthetic may be used separately or in combination with the biocompatible materials used to resurface the skin. Antibiotics could be included to prevent infection; bioabsorbable or biodegradable compounds or drugs can be delivered to the skin to treat diseases. Vasoconstrictors, such as adrenaline, can be placed into crystalline form and fired into the skin to constrict blood vessels on the surface of the skin to prevent bleeding. In addition vitamins including fat soluble (A, D, E, K) and water soluble vitamins (B complex, C), as well as co-enzymes, antioxidants, minerals, depigmenting medicines, antibiotics and other medicaments can be incorporated into the biocompatible materials.

In the present invention, the biocompatible materials are generated by abrading a solid frozen segment and propelling it through a delivery tip or nozzle to the surface of the skin or tissue to be treated. An optional vacuum system near the delivery tip can be used to remove excess materials or reaction by-products that build up on the surface of the skin. The biocompatible particles are produced at low enough temperatures to prevent the particle from melting during the delivery path to the tissue.

In one embodiment the treatment system consists of a control unit, a handheld particle generator and a cable that connects the control unit to the particle generator. The control unit can include user controls to select particle temperature, particle flux, particle velocity and vacuum. The handheld particle generator contains a mechanism to push a frozen block of biocompatible material against a rotating grinding wheel that produces small (<500 micron diameter) particles. The frozen block and grinding wheel temperature can be monitored with temperature sensors integrated into the handpiece. The temperature is controlled and kept below the melting temperature of the biocompatible material. The particle density can be adjusted by controlling the speed of the grinding wheel and the speed at which the frozen block is pushed toward the grinding wheel. In normal operation the user moves the handheld device over the surface to be treated. By adjusting the particle density, particle size and particle velocity a variety of effects can be achieved.

Optional infrared temperature sensors attached to the handheld device can be used to monitor surface temperature and guide the user through the treatment. Other possible sensors include particle density and particle velocity. An accurate measurement of the particle velocity and particle size can be used to estimate the penetration depth.

An objective of the present invention is to provide an apparatus to remove scars, wrinkles, and other imperfections of the skin (or other tissue) without introducing foreign bodies or substances that cause adverse physiological reactions or produce thermal damage. Another objective of the present invention is to provide an apparatus to clean wounds and perform burn debridement. Another objective of the invention is to provide a delivery system for delivering or depositing drugs or other medications at the desired depth in the epidermis or dermis for treatment of diseased skin lesions, e.g., pre-cancers. Other objects and advantages of the present invention will become apparent from the following description and accompanying drawings.

BRIEF DESCRIPTION OF THE DRAWINGS

The accompanying drawings, which are incorporated into and form part of this disclosure, illustrate embodiments of the invention and together with the description, serve to explain the principles of the invention.

DETAILED DESCRIPTION OF THE INVENTION

The present invention is an apparatus for resurfacing or treating tissue (e.g., skin) using biocompatible materials that are blasted/propelled at the tissue with sufficient velocity to cause destruction, loosening, or unbinding of tissues to the desired depth upon impact. The penetration depth of the particles is controlled by the operator. The materials that are propelled into the skin are non-toxic and are harmonious with the human body and thus do not cause foreign body reactions (which may lead to granulomatous disease and/or scarring). The materials must be hard enough (crystalline) or propelled forcefully enough to penetrate to the appropriate depth in the dermis to alter or remove unwanted skin features or tissue. Suitable materials include solid carbon dioxide (dry ice), ice (frozen $H_2O$), organic materials such as urea, or other amines (including amino acids) or amides, organic polymers such as sugars, carbohydrates, or proteins, and inorganic salts such as phosphates, sulfates, carbonates and nitrates. These materials can be used separately or in combination. Many other materials usable in the present invention are described below.

Several considerations are taken into account in the choice of skin resurfacing materials. Biocompatible materials are defined for purposes of this description as materials that can be propelled into the epidermal or dermal layers of the skin without a significant adverse biological (e.g., toxic, inflammatory, carcinogenic, or immunogenic) host response (e.g., foreign body reaction, autoimmune disease, necrosis, apoptosis) be it delayed or immediate. The propelled materials should be maintained in a solid form for maximal abrasive capability. The materials are preferably at low temperatures (e.g., <0° C.), although too cold of a material can result in unacceptable tissue death. Human tissues can safely tolerate freezing with ice to a certain extent, for a limited amount of time, before frostbite occurs. Other biocompatible materials or additives that have an additional function to impart to the skin can be used in combination with the resurfacing materials. These materials can also be imparted to the skin without the resurfacing materials. These additives may be particularly useful in cases where deeper tissue alteration is needed. For example, once the epidermis is penetrated by any surface destructive procedure, pain will result when the dermal nerves are stimulated. To relieve this pain, crystalline local anesthetic such as xylocaine (lidocaine) or many topical or local anesthetics could be used, either separately or in combination with other materials. These local anesthetics will dissolve and be carried to the dermal nerves upon impacting the skin. Additionally, vasoconstrictors or blood vessel closing agents such as adrenaline could be fired accompanying the carrier particles into the skin to constrict blood vessels on the surface of the skin to prevent bleeding, which is a common problem with many forms of skin resurfacing (e.g., dermabrasion, laser treatment). Less bleeding is especially desirable and needed if the resurfacing procedure is performed in the deeper skin levels. Buffering agents or hydrophilic materials to absorb surface fluids could also be useful, and antibiotics could be added to prevent infection.

The present invention may be used as a drug delivery system that provides bioabsorbable or biodegradable compounds or drugs by propelling them into the surface of the skin. Biodegradable polymeric systems can be used for drug delivery and offer greater flexibility in the design of delivery systems for large molecular weight drugs, such as peptides and proteins. Biocompatible gels, like hydrogels, can be grafted onto other biomaterials with good mechanical properties for skin resurfacing. The combination can accomplish both skin resurfacing and drug delivery in the epidermis and dermis. Water insoluble polymers such as poly(glycolic acid) have been investigated as biodegradable drug delivery systems.

For dermatological applications, the present invention may be used to deliver drugs for treatment of pre-cancerous or cancerous lesions in the epidermis and dermis. The topical delivery of certain medicines often cannot penetrate deeply or uniformly enough, and long-term topical application of the creams or gels is inconvenient for the patient. To achieve long-lasting, deeper skin treatment for lesions, drugs (e.g., 5-fluorouracil) in a crystal or gel form may be propelled with a carrier particle into the skin to penetrate the deep epidermis.

Figure 1:
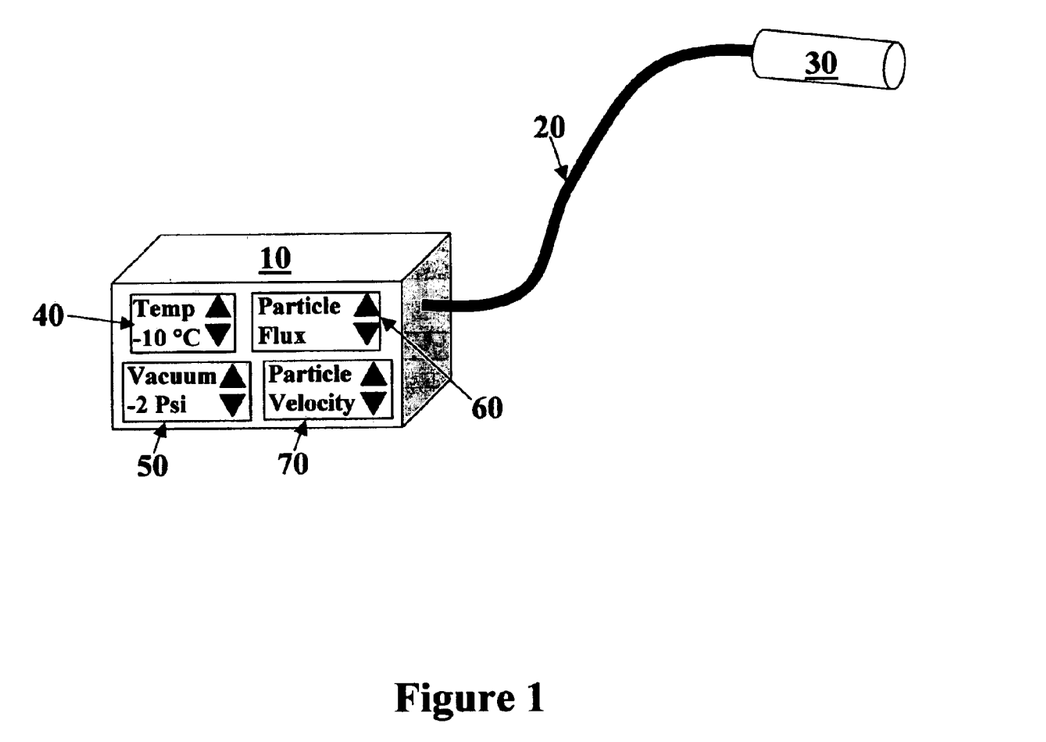
FIG. 1 shows one embodiment of the present invention where the control unit is connected to the handheld device by a cable.

FIG. 1 shows one embodiment of the present invention where the control unit 10 is connected to the handheld device 30 by a cable 20. The control unit 10 contains the necessary electronics to drive the motors within the handheld device 30 and monitor sensors within the handheld device. An optional vacuum pump within the control unit 10 connects through cable 20 to the handheld device and can be used to remove excess material or reaction by-products that build up on the surface of the skin. Adjusting the settings 60 on the control unit 10 can control the vacuum pressure. Additional controls 40, 50, 70 on the control unit 10 are used to control the operating parameters of the device. In normal use the handheld device 30 is scanned over the tissue to be treated.

Figure 2:
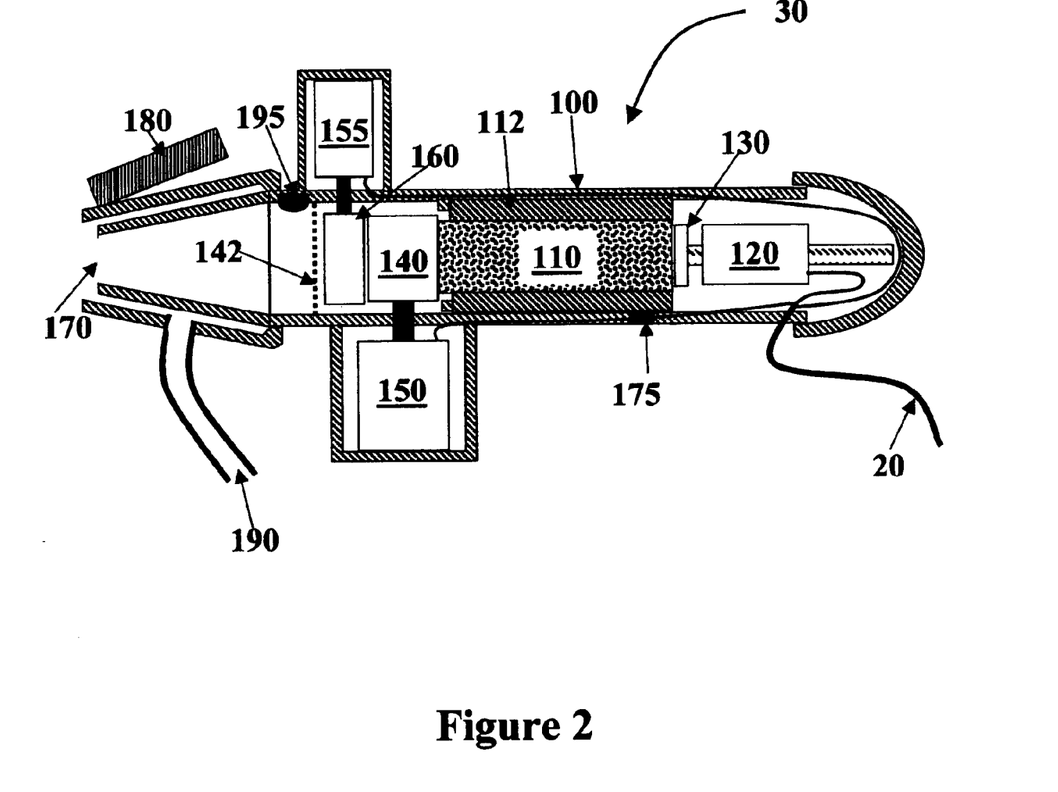
FIG. 2 shows a detailed cross-sectional view of one embodiment of the handheld device of the present invention.

FIG. 2 shows a detailed cross-sectional view of one embodiment of the handheld device 30. The handheld device consists of a housing 100 that is insulated to protect the user. An optional electric heater could be integrated into the outside wall of the device 30 to improve user comfort. A specially shaped frozen block of the biocompatible material (e.g., ice) 110 is located within the device 30. Biocompatible material 110 is within an insulating holder 112. The holder 112 can be part of the disposable cartridge used to prepare the frozen block and has a smooth inner surface to minimize friction. The most suitable material for the holder 112 is plastic (e.g. polyurethane, Teflon, or polyethylene). An electric motor 120 drives a piston 130 that pushes the block 110 onto a rotating grinder wheel 140 that is driven by a second electric motor 150. Electric motor 150 can be any small motor (e.g. MicroMo Electronics Inc. DC 1224 Series) with a suitable gearbox to rotate the grinder at rotation speeds greater than 10 RPM. The electric motors are powered and controlled through electrical wires that come from the control unit through the delivery tube/cable 20. The speed of the motors can be adjusted to control the particle density. The motors could also be powered pneumatically or by flexible cables connected to motors in the main control unit 10. As the rotating grinder wheel 140 rotates, biocompatible particles (e.g., ice) are produced then hit out of the device by spinning wheel 160 that is driven by motor 155. The particles exit device 30 through the exit aperture 170. The exit aperture 170 can be a variety of shapes including a narrow slit, rectangle, square, circle, or ellipse. An optional vacuum line 190 is used to pull debris, ice particles or water away from the surface. In order to maximize debris collection, the device 30 can be placed in contact with the surface to be treated. The final segment of device 30 can be made of clear plastic so that the user can easily see the surface and monitor progress.

A variety of possible designs can be used for the grinder wheel 140. In one embodiment the grinder wheel is made of surgical steel and has barbs on the surface to scrape off particles. An alternative design is a grinder wheel that consists of surgical steel wires that form a wire brush. Yet another grinder wheel design incorporates sharp cutting edges into the wheel that scrapes the solid block 110. An optional wire mesh 142 can be placed after the grinder wheel to prevent large particles from exiting the device and striking tissue.

An optional temperature sensor 175 monitors the holder 112 temperature to provide the user with a warning if the temperature approaches the melting temperature of the biocompatible block 110. Also, an optional infrared temperature sensor 180 can be incorporated into the device 30 to provide the user with the surface temperature of the area being treated. The measured surface temperature can be used by the user to prevent excessive cooling. Alternatively, the infrared temperature sensor 180 reading can be transmitted to the control unit and used to automatically turn off flow if the surface temperature drops below a preset limit An optional light source (e.g. LED) 195 can be used to send a beam of light to illuminate the particles as they move through the final stage. The light scattered by the particles can be seen by the user and provides confirmation that particles are flowing. In addition, an optional light detector filtered for the specific color of light used to illuminate the particles can be used to estimate particle density. In one embodiment the light detector would be positioned perpendicular to the light beam to minimize the collected light when no scattering particles were present. The control unit 10 could record the background detector signal just before starting particle generation. By subtracting this signal from that measured when particles are being generated an estimate of particle density could be calculated and displayed on the control unit 10.

The specially shaped block of biocompatible material 110 is prepared in a special mold by filling the mold with a mixture of water and any desired additives and then putting the mold in a freezer or liquid nitrogen dewar. By using sterile mixtures and molds, the risk of infection can be reduced.

Figure 3:
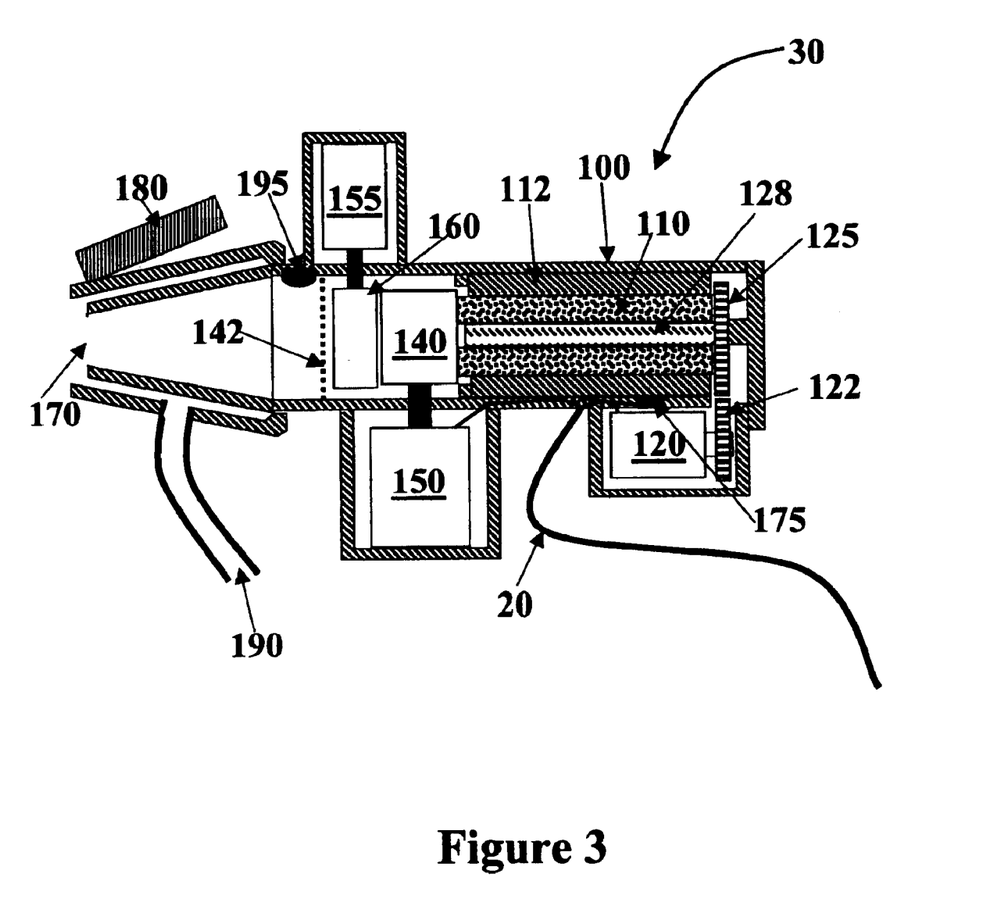
FIG. 3 shows a detailed cross-sectional view of an alternative embodiment of the handheld device of the present invention.
Figure 4A:
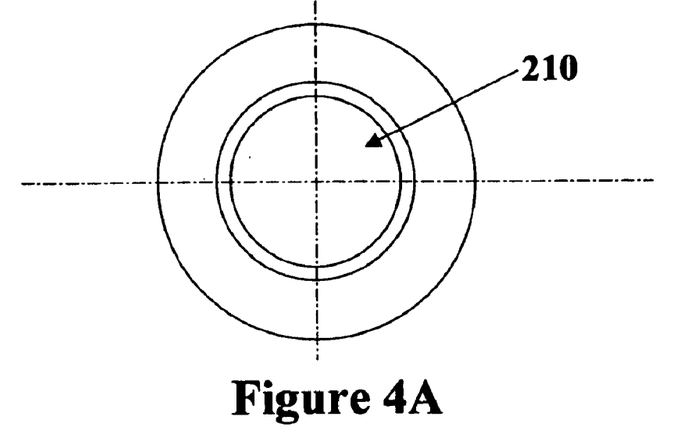
FIG. 4A shows a top view of a disposable cartridge used to produce the biocompatible solid.
Figure 4B:
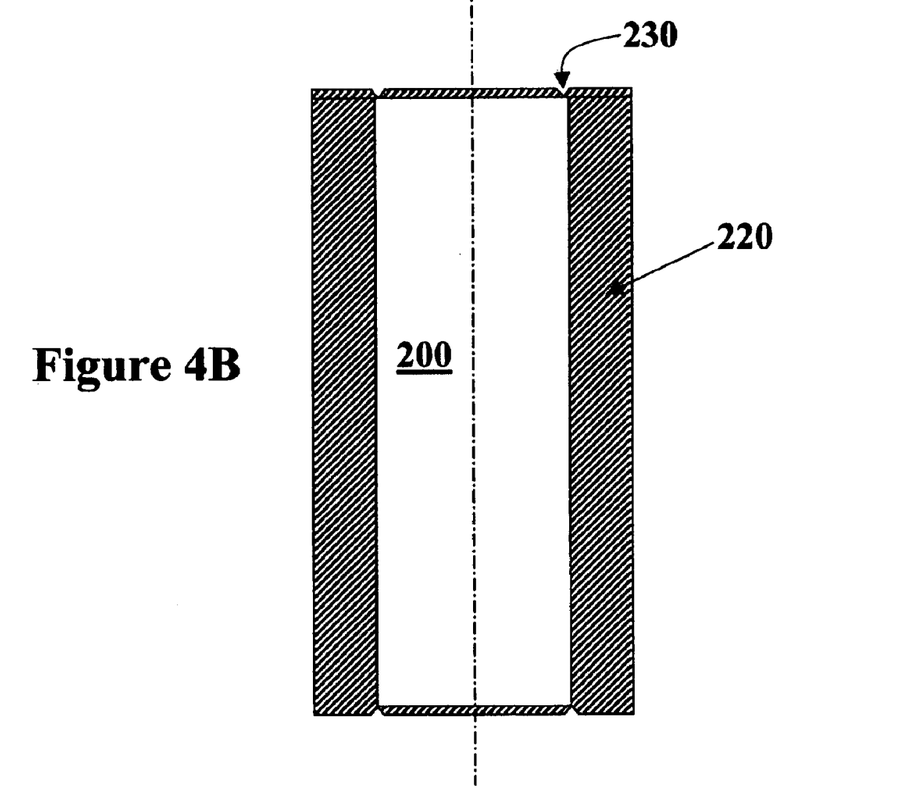
FIG. 4B shows a cross-sectional view of the disposable cartridge of FIG. 4A.
Figure 5A:
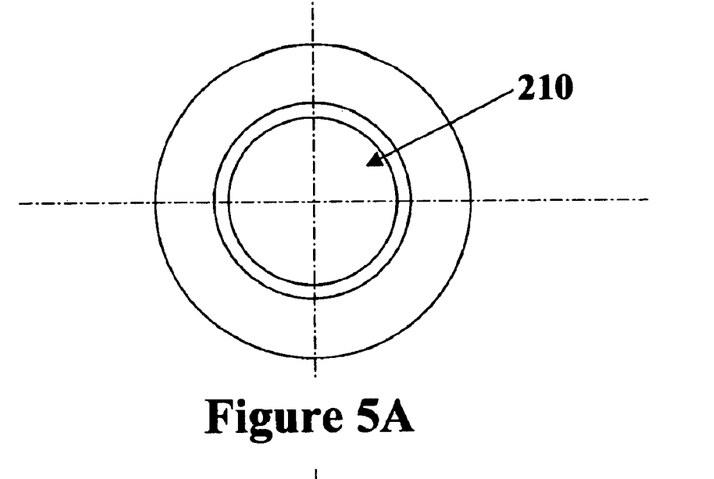
FIG. 5A shows a top view of an alternative disposable cartridge used to produce the biocompatible solid.
Figure 5B:
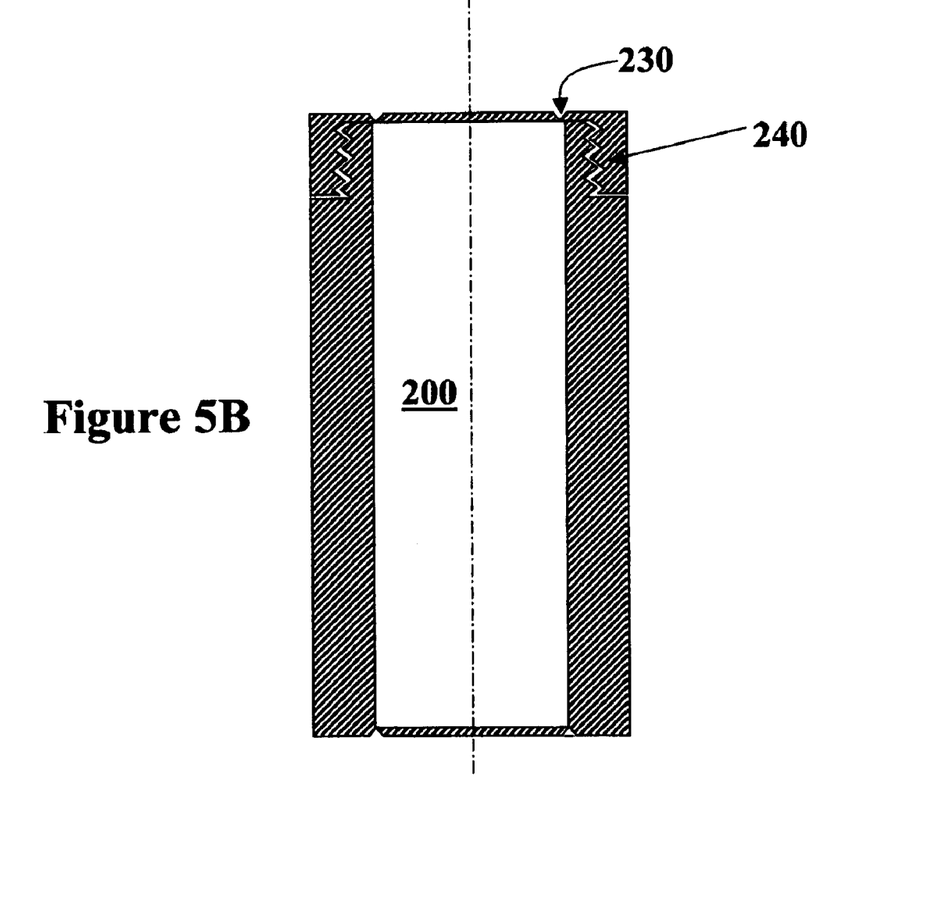
FIG. 5B shows a cross-sectional view of the disposable cartridge of FIG. 5A.

FIG. 3 shows a detailed cross-sectional view of an alternative embodiment of the handheld device 30. In this embodiment the biocompatible material 110 is formed around a threaded shaft 128 that is turned by motor 120 through gears 122 and 125. As the shaft 128 rotates the biocompatible material 110 is pushed into the grinding wheel 140. This embodiment allows for a shorter and lighter device.

FIGS. 4A through 7B show different embodiments of a disposable cartridge used to prepare the frozen biocompatible material. The cartridges are prefilled with liquid and then placed in a controlled environment to freeze the liquid 200. Once frozen the cartridge can be removed and the end caps 210 torn off along indentation 230. The outer wall of the cartridge 220 is thick enough to insure that the frozen material does not melt during use. In the embodiment of FIGS. 5A and 5B, one end cap 240 screws onto the cartridge and is locked in position after filling the cartridge with liquid. The advantage of this embodiment is that it makes filling the cartridge easier.

Figure 6A:
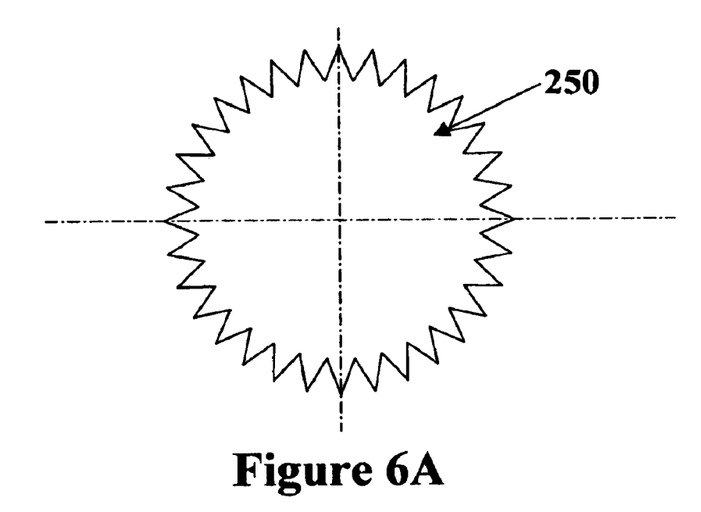
FIG. 6A shows a top view of an alternative disposable cartridge used to produce the biocompatible solid.
Figure 6B:
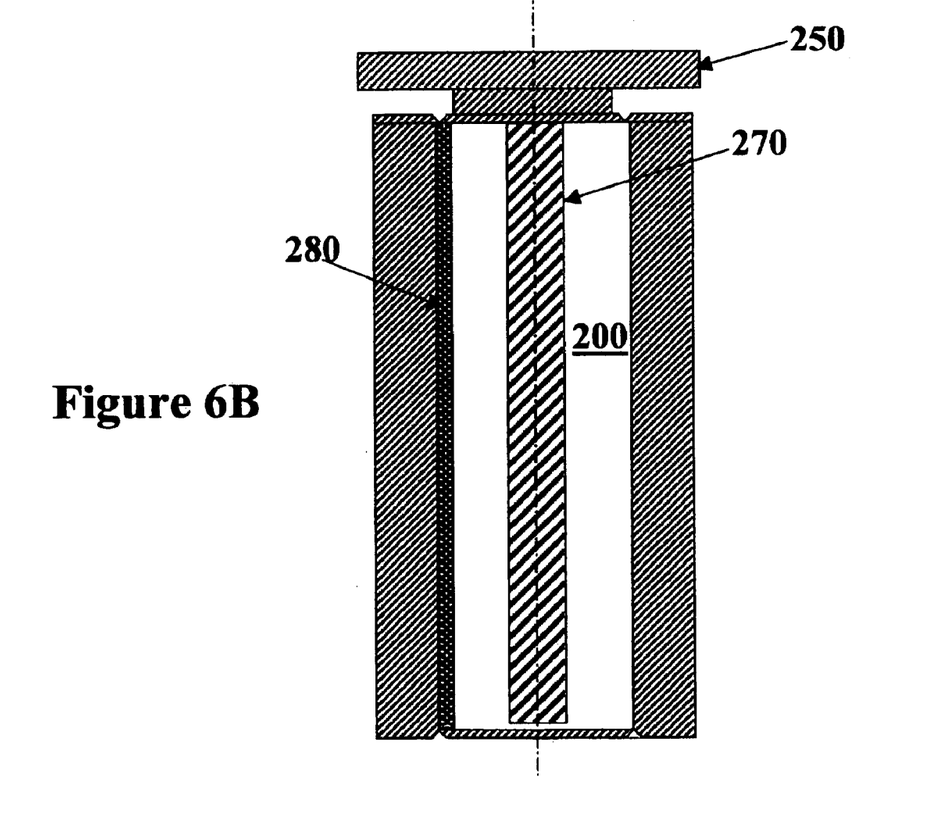
FIG. 6B shows a cross-sectional view of the disposable cartridge of FIG. 6A.
Figure 7A:
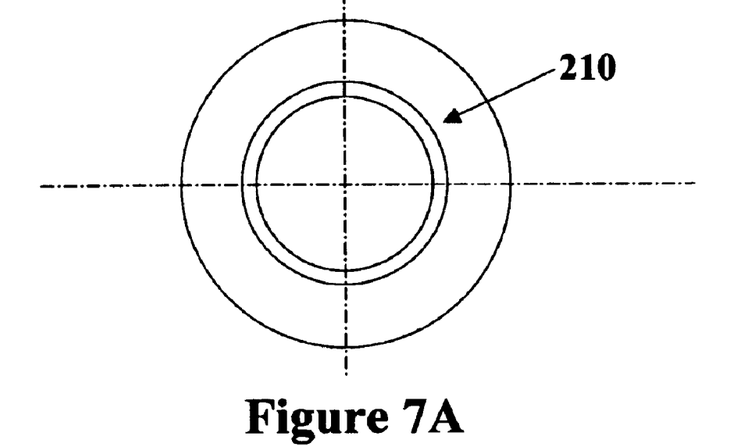
FIG. 7A shows a top view of an alternative disposable cartridge used to produce the biocompatible solid.
Figure 7B:
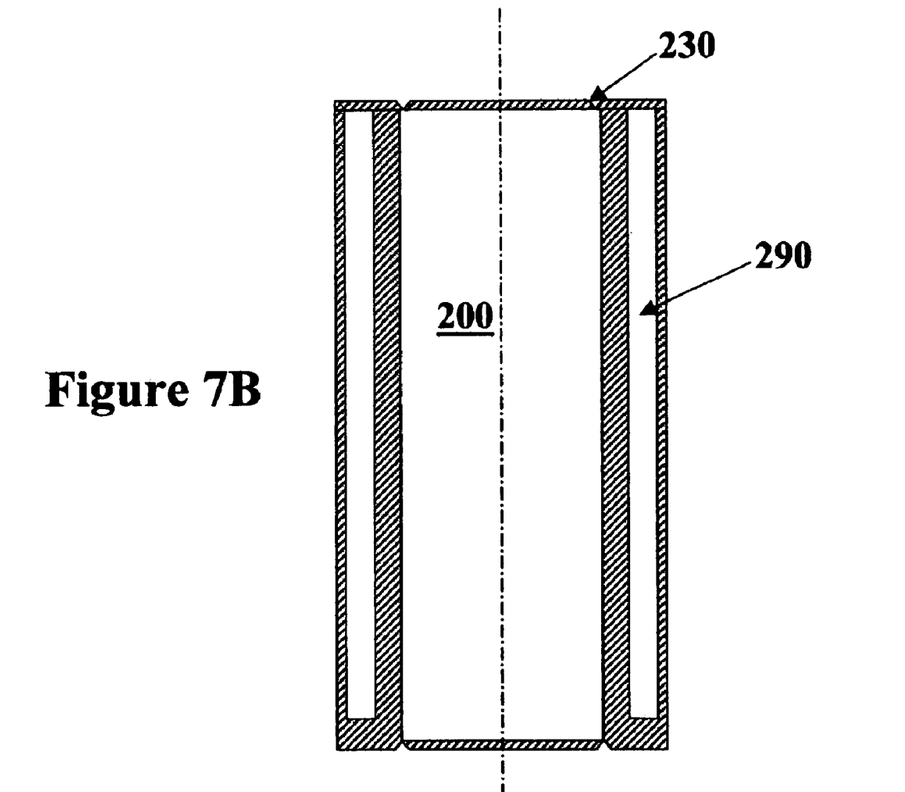
FIG. 7B shows a cross-sectional view of the disposable cartridge of FIG. 7A.

FIGS. 6A and 6B show an embodiment in which a threaded shaft 270 that connects to a gear 250 is frozen within the block. An indentation 280 within the cartridge keeps the frozen block 200 from rotating as the threaded shaft is rotated. In this way the frozen block is pushed out the cartridge. This embodiment could be used in the embodiment of FIG. 3. FIGS. 7A and 7B show an alternative embodiment of the cartridge that includes an air layer 290 to insulate the frozen block 200.

Figure 8:
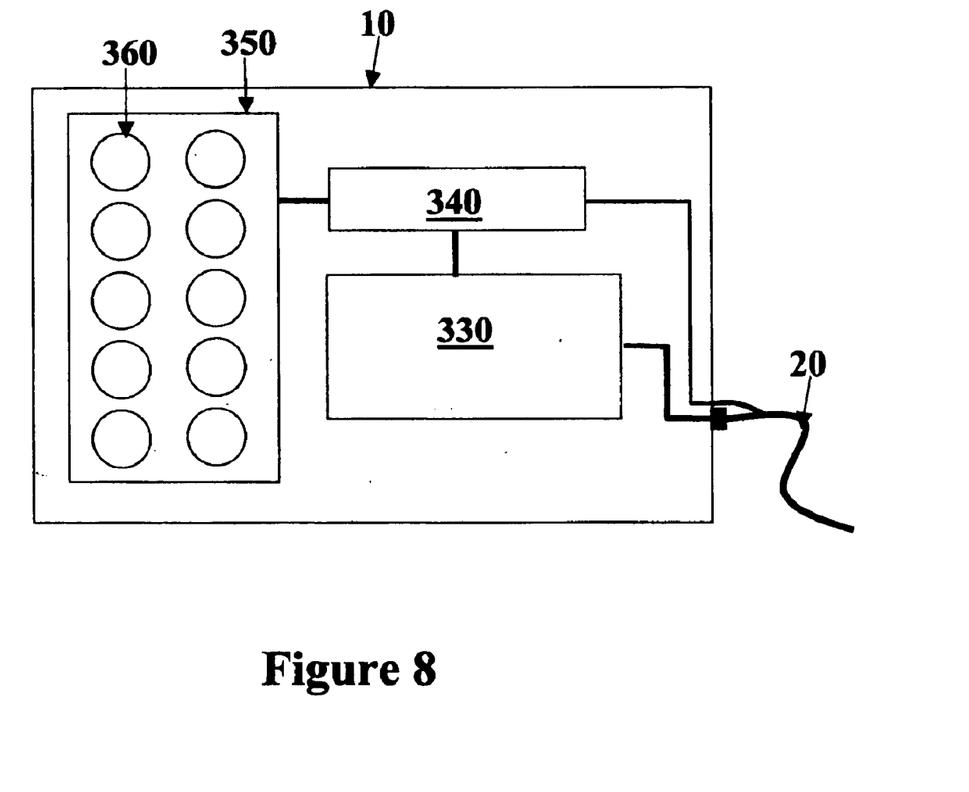
FIG. 8 shows a block diagram of the key components of the control unit.

FIG. 8 shows a block diagram of the key components of the control unit 10. The control unit 10 includes control electronics 340 that power all motors within the handheld device and monitor sensors. The control electronics further control the optional vacuum pump 330 and cartridge freezer 350. The user can load cartridges filled with biocompatible material into receptacles 360. The temperature controlled freezer 350 cools the cartridge and freezes the biocompatible liquid. The user removes the frozen cartridge and removes the endcaps before loading it into the handheld device 30. User input devices such as knobs, or push buttons on the control unit can be used to adjust the operation of the control unit and device. An optional LCD or other electronic screen on the control unit 10 can provide the user with the current settings and actual readings from sensors on the device 30.

The delivery apparatus may also include an attachment to measure the surface temperature of the skin using an infrared sensor or direct thermocouple (See sensor 180 in FIG. 2). Additionally, the delivery apparatus may include pressure sensitive sensors (e.g., spring-loaded) that allow the operator to sense and alter contour by hand-pressure. Such a device can be applied to the delivery tip, so the more pressure the operator applies, the greater the velocity and volume of shooting particles that are delivered to a certain area. Applying differential pressure is advantageous to reduce a tissue mound, lip, or edge with feedback just by operator feel.

A feedback sensor (e.g., optical) may be used to monitor the penetration depth of particles at the skin surface. One possible optical technique that could be incorporated into the system is optical coherence tomography (OCT or OCDR). This optical technique can image several millimeters into tissue and provide the user with information about how tissue is being removed. The operator may be alerted by a series of audible sounds as to how fast to move the tip for maximum efficiency on a particular patient's skin. Maximum efficiency is based on the skin temperature, particle load and velocity, and type of particle shot at the skin.

Companion and Integral Chemicals

Companion-Chemicals and classifications of substances that may be used to comprise a frozen cutaneous projectile are:

Steroids including betamethasone, hydrocortisone and cortisone derivatives;

Salts including sodium chloride and calcium chloride buffers including sodium bicarbonate and phosphates;

Antifreezes such as polyethylene glycol;

Antipsoriasis drugs such as dovonex, tazarotene, tars, steroids;

Pigmenters/coloring agents including dihydroxyacetone, melanin, hemoglobin or hemosiderin; Mineral coloring agents including iron and copper;

Depigmenters including hydroquinones, and phenolic compounds;

Tattooing or body artistry including airbrushing with oil and water-soluble skin dyes;

Fat-soluble vitamins including A, D, E, K;

Water-soluble vitamins including B complex and C;

Minerals including iron, selenium, calcium, and magnesium;

Dyes including vegetable: carrots, beets, wildflowers, native American Indian dyes, berries;

Dyes, especially fluorescent;

Preservatives including benzoates, parabens and salicylates;

Antioxidants including Coenzyme Q and Vitamin E and salicylic acid;

Anesthetics including xylocaine, bupivicane, carbocane, all amide and ester-based-local-anesthetics (as well as all remaining local and topical anesthetics);

Vasoconstrictors including epinephrine and ephedrine and congeners thereof;

Alpha-hydroxy acids, Beta-hydroxy acids, halogenated acetic acids, other peeling acids;

Irritants including acids, croton oil, and soaps including salts of fatty acids;

Antibiotics, e.g., penicillin, amoxicillin, erythromycin, tetracycline, monocycline, minocycline, mupirocin, flagyl, ciprofloxacin, polymixin, gentamycin and other antibacterials;

Antivirals including acyclovir, famciclovir, valtrex, etc.;

Antifungals including imidazoles, nystatin, and griseofulvin, and sporonox;

Depilatories such as eflornithine hydrochloride;

Co-enzymes;

Proanthrocyanins such as maritime pine extract (Pycnogenol™); tocopheryl acetate;

Vitamin A precursors; and

Microparticles (lactic-glycolic acid) and microspheres and liposomes and proteins (such as albumin) with relative stability in ice. The present invention can propel into the skin any of the materials mentioned in this section, as well as propel into the skin virtually any other medicine known to man.

For drugs that are oil-soluble or poorly soluble in water then these compounds can be carried by microparticles (lactic-glycolic acid), microspheres, liposomes and proteins (such as albumin) that have relative stability in ice. These structures may be fabricated biochemically to coat and therefore contain any of the materials/drugs/vitamins/minerals/anesthetics/pigments mentioned in this section and virtually any other medicine known to man. These structures are a bit fat-soluble and are able to penetrate deeply into the skin by being handed from oil-soluble to oil-soluble layer. All of the above can come in premixed plastic cartridges that can be frozen and put into the ice-blasting gun. Or they can be mixed by the doctor/nurse on site, frozen in a mold and placed into the gun without a plastic jacket or sleeve or cartridge.

The foregoing description of preferred embodiments of the invention is presented for purposes of illustration and description and is not intended to be exhaustive or to limit the invention to the precise form disclosed. Many modifications and variations are possible in light of the above teaching.

What is claimed is:

1. A treatment apparatus, comprising:
   a housing operatively and electrically connected to a control unit;
   means, within said housing, for removing material from a frozen cartridge of biocompatible material to produce particles; and
   means for ejecting said particles from said housing.

2. The apparatus of claim 1, further comprising said frozen cartridge of biocompatible material operatively positioned within said housing.

3. The apparatus of claim 2, further comprising insulation located between said frozen cartridge and the inner wall of said housing.

4. The apparatus of claim 2, wherein said frozen unit is formed in a cartridge.

5. The apparatus of claim 4, wherein said cartridge is disposable.

6. The apparatus of claim 4, wherein said cartridge comprises a cylinder with an endcap on each end of said cylinder, wherein each endcap comprises an indentation, wherein said endcap is removable at said indentation.

7. The apparatus of claim 4, wherein said cartridge comprises a threaded endcap.

8. The apparatus of claim 4, wherein said cartridge comprises a threaded shaft that connects to a gear, wherein said threaded shaft is positioned to be frozen within said frozen unit.

9. The apparatus of claim 8, wherein said cartridge further comprises an indentation to keep said frozen unit from rotating when said threaded shaft is rotated.

10. The apparatus of claim 4, wherein said cartridge comprises an outer insulation layer.

11. The apparatus of claim 10, wherein said insulation layer comprises an air layer.

12. The apparatus of claim 4, wherein said control unit comprises a freezer to freeze or keep frozen said frozen unit within said cartridge.

13. The apparatus of claim 1, wherein said control unit comprises means for controlling said means for removing material from said frozen cartridge.

14. The apparatus of claim 1, wherein said control unit comprises means for controlling said means for ejecting said particles from said housing.

15. The apparatus of claim 1, wherein said housing is configured to be held in a user's hand.

16. The apparatus of claim 1, wherein said housing comprises a temperature sensor for measuring the temperature of said housing, wherein said control unit controls and reads said temperature sensor and provides a user with a warning if said temperature approaches the melting temperature of said frozen cartridge.

17. The apparatus of claim 1, further comprising a particle sensor fixedly attached to said housing, wherein said particle sensor is controlled and monitored by said control unit.

18. The apparatus of claim 17, wherein said particle sensor comprises a light source to send a beam of light to illuminate said particles as they move between said means for removing material and said aperture.

19. The apparatus of claim 18, wherein said light source comprises a light emitting diode.

20. The apparatus of claim 18, further comprising a light detector filtered for the specific color of light used to illuminate said particles.

21. The apparatus of claim 1, further comprising a temperature sensor fixedly attached to said housing, wherein said temperature sensor is operatively positioned to read the temperature of a surface against which said particles are directed after said particles are ejected from said housing.

22. The apparatus of claim 21, wherein said temperature sensor comprises an infrared temperature sensor to provide the user with the surface temperature of said surface.

23. The apparatus of claim 22, wherein said control unit includes means for turning off said means for removing material and said means for ejecting said particles if the temperature of said surface drops below a preset limit.

24. The apparatus of claim 1, further comprising a vacuum line connected to said housing to remove material from said housing, wherein said vacuum line is operatively connected to and controlled by said control unit, wherein said control unit comprises a vacuum system.

25. The apparatus of claim 1, wherein said means for removing material comprises a cutting mechanism to cut particles from said frozen cartridge, wherein said means for removing material further comprises means for forcing said frozen cartridge against said cutting mechanism.

26. The apparatus of claim 25, wherein said cutting mechanism comprises a rotating grinder wheel driven by an electric motor.

27. The apparatus of claim 26, wherein said rotating grinder wheel comprises surgical steel and has surface barbs to scrape off said particles.

28. The apparatus of claim 26, wherein said rotating grinder wheel comprises surgical steel wires that form a wire brush.

29. The apparatus of claim 26, wherein said rotating grinder wheel comprises sharp cutting edges that scrapes said particles from said frozen cartridge.

30. The apparatus of claim 26, wherein said means for removing material from said frozen unit comprises a threaded shaft attached to a gear that is operatively positioned next to a motor driven gear that will rotate said threaded shaft when said motor driven gear turns, wherein said frozen unit is formed onto said threaded shaft, said apparatus further comprising means for preventing said frozen unit from rotating as said threaded shaft is rotated, wherein said frozen unit is pushed into said grinding wheel.

31. The apparatus of claim 25, wherein said means for forcing said frozen cartridge against said cutting mechanism comprises an electric motor that drives a piston that pushes said frozen cartridge into said cutting mechanism.

32. The apparatus of claim 25, wherein said means for removing material comprises means for adjusting the density of said particles.

33. The apparatus of claim 1, wherein said means for ejecting said particles from said housing comprises a spinning wheel that is driven by an electric motor.

34. The apparatus of claim 1, wherein said housing comprises an exit aperture that comprises a shape selected from the group consisting of a narrow slit, a rectangle, a square, a circle and an ellipse.

35. The apparatus of claim 1, wherein said housing comprises a window having optically clear material so that a user can see a treatment surface and monitor progress.

36. The apparatus of claim 1, further comprising means for ejecting said particles to prevent large particles from exiting said housing and striking a surface under treatment.

37. The apparatus of claim 1, wherein said housing further comprises a pressure sensitive sensor operatively connected to said control unit to adjust the amount of said particles ejected from said aperture to allow a user to sense and alter the contour of a treatment surface by hand-pressure.

38. The apparatus of claim 1, wherein said housing further comprises a treatment depth sensor.

39. The apparatus of claim 38, wherein said treatment depth sensor comprises an optical coherence tomography system.

* * * * *